United States Patent
Franzreb et al.

(10) Patent No.: US 6,942,806 B2
(45) Date of Patent: Sep. 13, 2005

(54) METHOD FOR SEPARATING A DISPERSED OR DISSOLVED SUBSTANCE AND MAGNET SEPARATOR

(75) Inventors: Matthias Franzreb, Karlsruhe (DE); Jonas Wohlgemuth, Rheinsheim (DE)

(73) Assignee: Forschungszentrum Karlsruhe GmbH, Karlsruhe (DE)

(*) Notice: Subject to any disclaimer, the term of this patent is extended or adjusted under 35 U.S.C. 154(b) by 0 days.

(21) Appl. No.: 10/432,030

(22) PCT Filed: Oct. 12, 2001

(86) PCT No.: PCT/EP01/11807
§ 371 (c)(1),
(2), (4) Date: Sep. 17, 2003

(87) PCT Pub. No.: WO02/40173
PCT Pub. Date: May 23, 2002

(65) Prior Publication Data
US 2004/0029291 A1 Feb. 12, 2004

(30) Foreign Application Priority Data
Nov. 18, 2000 (DE) .......................................... 100 57 396

(51) Int. Cl.⁷ .............................. B03C 1/28; G01N 1/18
(52) U.S. Cl. ....................... 210/695; 210/222; 209/226; 436/177; 436/526; 435/287.3; 422/101
(58) Field of Search ................................ 436/177, 526, 436/287.3; 422/101; 210/222, 695; 209/226

(56) References Cited

U.S. PATENT DOCUMENTS 4,751,053 A * 6/1988 Dodin et al. ................. 422/101
6,040,192 A * 3/2000 Tuunanen ..................... 436/177

FOREIGN PATENT DOCUMENTS

| DE | 44 21 058 A1 | 12/1995 |
| DE | 197 30 497 A | 2/1999 |
| EP | 0 181 798 A | 5/1986 |
| WO | WO 92/04961 A1 | 4/1992 |

* cited by examiner

Primary Examiner—David A. Reifsnyder
(74) Attorney, Agent, or Firm—Venable, LLP; Robert Kinberg; Thomas G. Wiseman

(57) ABSTRACT

The invention relates to a method for separating out a substance dispersed or dissolved in a first liquid by using the following steps:

Figure 1:
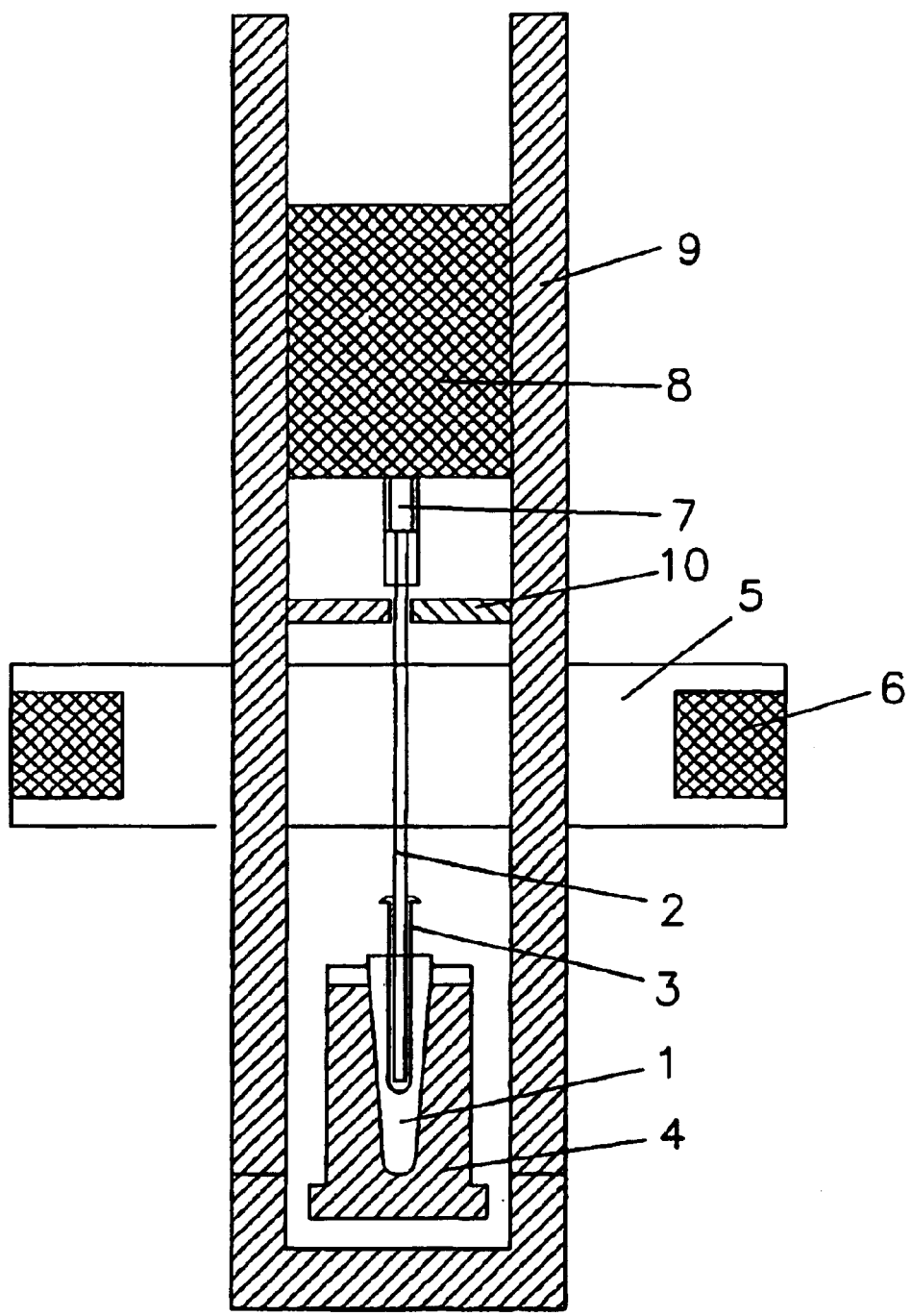

a) adding magnetizable particles to the first liquid, so that the substance is adsorbed on the particles;
b) immersing a rod consisting of a soft magnetic material into the first liquid;
c) magnetizing the rod along its longitudinal axis with an exciter coil, thus causing the particles with the adsorbed substance to be deposited on the rod;
d) pulling the rod with thereon deposited particles from the first liquid while the rod is still magnetized;
e) immersing the rod into a second liquid;
f) turning off the exciter coil and washing off the particles deposited on the rod in the second liquid.

Also proposed is a magnet separator for realizing the method.

4 Claims, 3 Drawing Sheets

METHOD FOR SEPARATING A DISPERSED OR DISSOLVED SUBSTANCE AND MAGNET SEPARATOR

The invention relates to a method for separating out and converting a dispersed or dissolved substance according to claim 1 and a magnet separator as defined in claim 3.

The problem of separating out biological material that is present in small amounts from blood or urine samples, to remove impurities and subsequently perform a qualitative and/or quantitative analysis frequently comes up in the field of medical diagnostics. In the process, the biological material is first bound to functionalized magnetizable micro-particles and is then separated out together with these particles, wherein the magnetizable micro-particles are fixated with the aid of electrical or magnetic fields. An antibody, for example, that binds the material of interest with high selectivity can serve as functional group for this process. The charged, magnetizable micro-particles are subsequently brought in contact with a new liquid, e.g. for the purpose of washing or eluting the material. Other areas of biotechnology are also faced with similar separation tasks. With a corresponding functionalizing of the micro-particles, it is possible to easily separate cells, proteins, nucleic acid sequences, bacteria such as yeast etc. from the various distillates.

Magnetizable micro-particles can be used as adsorbing agents for separating out these constituents while magnet separators can be used for depositing them. Correspondingly functionalized magnetic micro-particles have been commercially available since the 80's.

A method for separating out dispersed or dissolved substances as well as a magnet separator are known from U.S. Pat. No. 6,040,192. This method uses a vertically arranged, hollow rod with a vertically displaceable permanent magnet disposed on the inside. The two poles of the magnet are arranged along the longitudinal axis of the rod. The rod is immersed into a liquid containing magnetizable particles, with the permanent magnet disposed at the lower end of the rod, and is subsequently pulled from the liquid together with the adhering particles. The adhering particles can be washed from the rod by immersing the rod into an eluting solution and pushing the permanent magnet toward the top. The rod is moved up and down along its longitudinal axis for a thorough mixing of the liquid and eluting solution.
"

A description of this method and the magnet separator can also be found on the Internet (http://www.thescientest.com/yr2000/jun/profile1_000626.html)."has been deleted.

The disadvantage of the aforementioned method and magnet separator is that the magnetic field cannot be controlled and can be changed at the sample location only through mechanical displacement of the permanent magnet. This can cause problems during the elution or the re-suspension of already deposited particles because permanent agglomerations of particles due to interaction between particles can occur as a result of selecting unfavorable magnetic fields, even if the outer magnetic field has been removed. These agglomerations form as a result of van der Waals forces, for example, through cross-linking of long-chain bio-molecules or residual magnetism of the particles after the separation. It should therefore be possible to adapt the magnetic field intensity to the respective separation task. Another problem is that permanent magnets make further miniaturization more difficult. A precondition of modem analysis and screening methods often is the parallel processing of 96 or even 384 sample volumes in micro-titration plates. In addition, the method for mixing the liquid is not very effective and is therefore time-consuming.

It is the object of the invention to propose a method and a magnet separator without these disadvantages, for which particularly the magnetic field can be adjusted to a desired value and the mixing operation can be made more effective.

This object is solved as described in claims 1 and 3. Preferred embodiments of the method and the magnet separator are described in the remaining claims.

According to the proposed method, magnetizable particles are added to the solution or dispersion of a substance, which are selected such that the substance is adsorbed on the particles. Particles suitable for bio-molecules such as DNS [deoxyribonucleic acid], RNS [ribonucleic acid], for proteins or for cells such as blood cells are sold commercially. Generally suitable for use are particles composed of magnetite ($Fe_3O_4$) or chromium dioxide ($CrO_2$), which are coated for example with bifunctional organic silanes and have a large outer surface, or functionalized particles composed of polyvinyl alcohols or aginate, for example, which contain embedded magnetite, maghemite or chromium dioxide particles. The particle size can range from 50 nm to 500 $\mu$m and is preferably between 0.1 $\mu$m and 10 $\mu$m. The amount used is based on the amount of the substance to be separated out.

A rod made of a soft magnetic material is then immersed into the solution or dispersion containing the magnetizable particles. Soft iron or steel of the type DIN 1.4016 in particular can be used for the soft magnetic material. Direct contact between the soft-magnetic material and the solution or dispersion and thus the magnetizable particles can be avoided if the rod is provided with a protective covering, for example a plastic coating. Polyethylene, polypropylene or polystyrene in particularly is suitable as material for the protective covering. The material and the material thickness of the protective covering must be selected such that it does not significantly influence the magnetic field.

The rod can be made to rotate around its longitudinal axis for a thorough mixing of the solution or dispersion. As a rule, a rotational speed of 1 to 50 rotations per second results in an effective mixing.

In the following method step, the rod is magnetized along its longitudinal axis. An electromagnetic exciter coil that surrounds the rod in a suitable manner is used for the magnetizing. The maximum magnetic field of the coil should be between 2 and 100 m Tesla, wherein a coil is preferably used, which makes it easy to adjust the magnetic field to an optimum value. The magnetizing of the rod causes the magnetizable particles with the adsorbed substance to be deposited on the rod. The particle deposit can be aided by rotating the rod slowly around its longitudinal axis, preferably at 0.1 to 5 rotations per second.

The rod with the particles deposited thereon is then pulled in longitudinal axis direction from the solution or dispersion while the magnetic field remains activated so that the particles continue to adhere to the rod. If the rod was rotating prior to removal, this rotation is stopped.

The rod is then immersed into a second vessel containing a different liquid, in which the particles are dispersed. The magnetic field is turned off for this and the particles adhering to the rod are washed off. In the process, the rod is made to rotate rapidly around its longitudinal axis, e.g. at 1 to 50 rotations per second. This rotation is very effective for removing the deposited particles from the rod.

If the adhering particles with the adsorbed substance are to be rejected, the rod can alternatively be simply sprayed off with the liquid while the exciter coil is turned off and the rod is set to a fast rotation.

Several exemplary embodiments of the magnet separator are explained in the following in further detail and with the aid of three Figures:

Shown are in:

FIG. 1 A first exemplary embodiment with a single rod.

Figure 2:
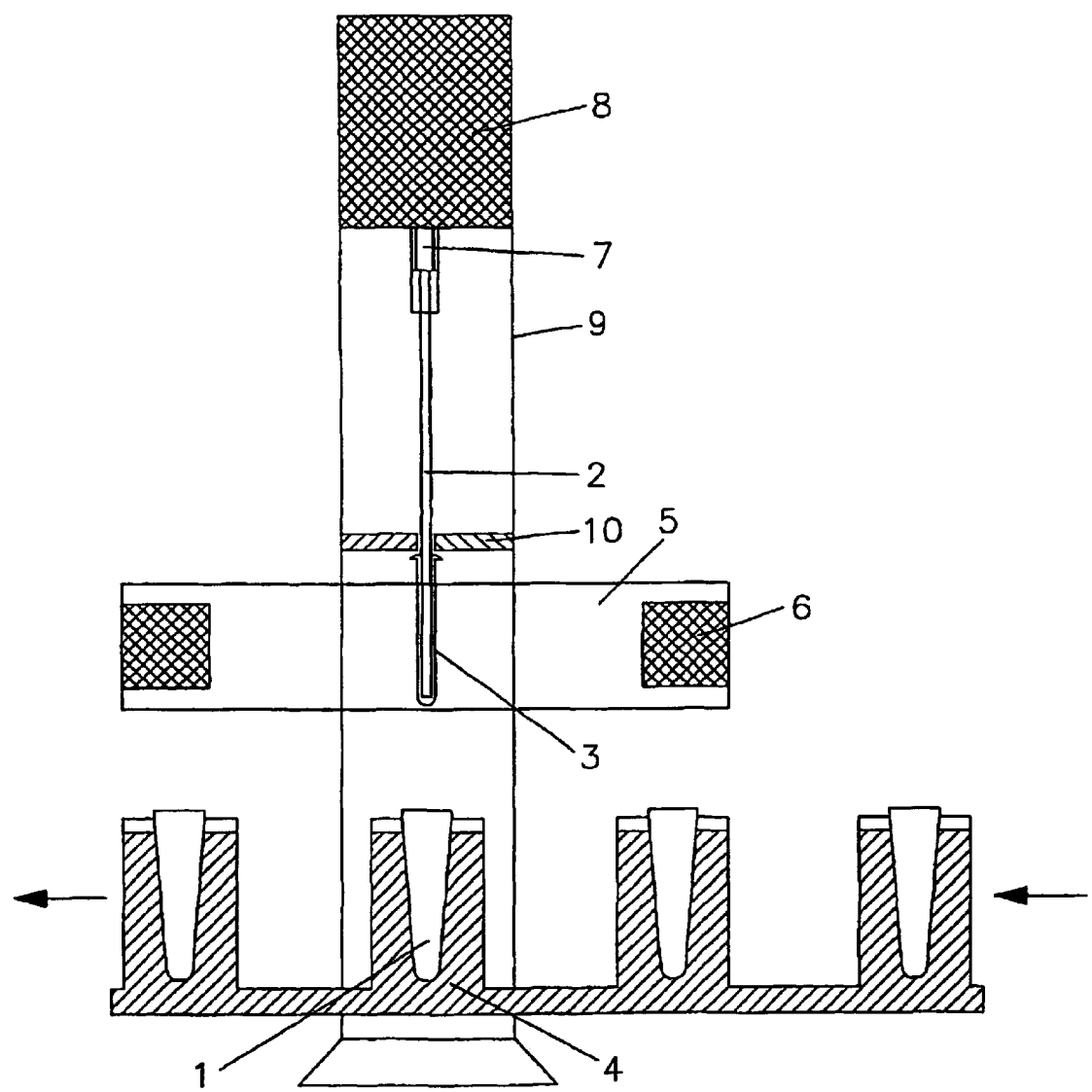

FIG. 2 A second exemplary embodiment with a single rod and displaceable sample holders.

Figure 3:
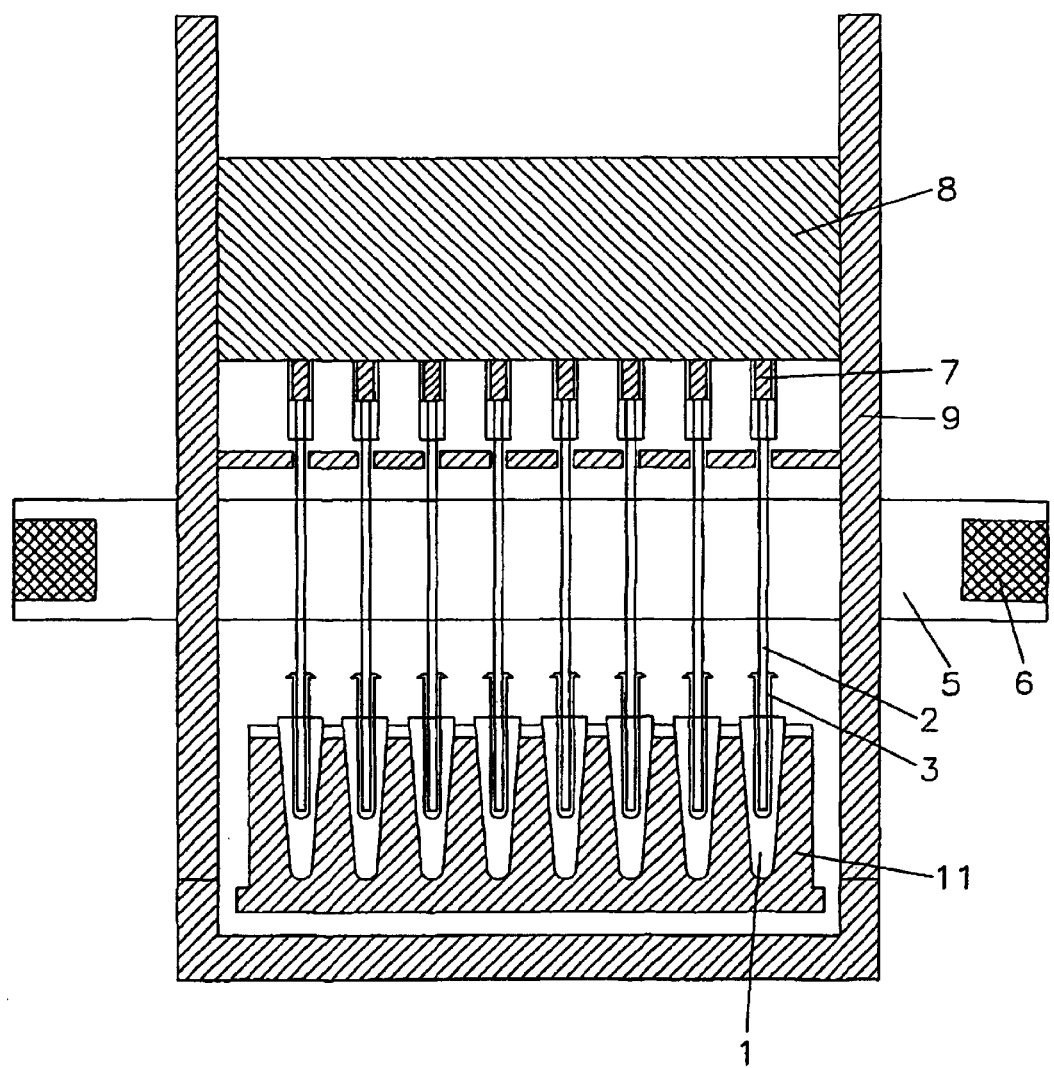

FIG. 3 A third exemplary embodiment with several rods and sample holders.

FIG. 1 shows a magnet separator having a single rod 2 of a soft magnetic material. The rod 2 is immersed into the liquid 1 in which magnetizable particles are dispersed. The rod 2 is provided with a replaceable covering 3 of plastic, which prevents direct contact between the soft-magnetic material and the liquid 1 as well as its constituents. The vessel containing the liquid is inserted into the holder 4. A coil holder 5 with an electromagnetic exciter coil 6 is arranged around the rod 2 and is used to magnetize the rod 2 along its longitudinal axis. The free end of the rod 2 is positioned in a holder 8 that is vertically displaceable inside the housing 9 and is furthermore provided with a device 7 for rotating the rod at a slow as well as a fast rotational speed. The housing 9 is additionally provided with an aperture 10 on which the covering 3 can be stripped off.

FIG. 2 shows another embodiment, which differs from the embodiment shown in FIG. 1 in that a holder 4 is designed to hold several samples simultaneously. The holder 4 is horizontally displaceable, so that the rod 2 can be immersed into each liquid 1. The remaining reference numbers have the same meaning as in FIG. 1.

FIG. 3 shows a device with a plurality of rods 2 and a horizontally displaceable holder 11 for a plurality of vessels containing liquids 1. An embodiment of this type permits the automated processing of samples. The reference numbers again have the same meaning as in FIG. 1.

What is claimed is:

1. A method for separating out a substance that is dispersed or dissolved in a first liquid by using the following steps:
   a) adding magnetizable particles to the first liquid, such that the substance can be adsorbed on the particles;
   b) immersing a rod consisting of a soft magnetic material into the first liquid;
   c) magnetizing the rod along its longitudinal axis with an exciter coil, which causes the particles with the adsorbed substance to be deposited on the rod;
   d) pulling the rod with thereon deposited particles from the first liquid while the rod is still magnetized;
   e) turning off the exciter coil and washing the deposited particles from the rod with the aid of a second liquid while the rod is rotating around its longitudinal axis.

2. The method according to claim 1, for which the first liquid is thoroughly mixed by rotating the rod around its longitudinal axis.

3. A magnet separator for separating out a substance that is dispersed or dissolved in a first liquid, said magnet separator having the following features:
   a) at least one vertically arranged rod of a soft magnetic material with a lower and an upper end is secured with its upper end in a holder, such that it can be moved along its longitudinal axis and can be made to rotate around its longitudinal axis in a controlled manner by means provided within the holder;
   b) the rod is surrounded by an electric exciter coil, which is arranged such that it can be magnetized by activating the exciter coil along its longitudinal axis.

4. The magnet separator according to claim 3 for which the lower end of the rod is surrounded by a plastic covering.

* * * * *